United States Patent [19]

Willner et al.

[11] Patent Number: 4,827,134
[45] Date of Patent: May 2, 1989

[54] DEVICE FOR COLLECTING SAMPLES

[75] Inventors: Helge Willner, Seelze; Arno Simon, Karlsruhe, both of Fed. Rep. of Germany

[73] Assignee: Bruker Analytische Messtechnik GmbH, Fed. Rep. of Germany

[21] Appl. No.: 119,704

[22] Filed: Nov. 12, 1987

[30] Foreign Application Priority Data

Nov. 15, 1986 [DE] Fed. Rep. of Germany ....... 3639105

[51] Int. Cl.[4] .......................................... G01N 21/00
[52] U.S. Cl. .................................... 250/352; 250/341
[58] Field of Search .................. 250/352, 341; 356/36

[56] References Cited

U.S. PATENT DOCUMENTS

| 4,158,772 | 6/1979 | Reedy | 250/338 |
| 4,218,892 | 8/1980 | Stephens | 62/514 R |
| 4,594,226 | 6/1986 | Reedy | 422/89 |
| 4,688,936 | 8/1987 | Reedy | 356/36 |

FOREIGN PATENT DOCUMENTS 210348  6/1984  German Democratic Rep. ... 356/36

OTHER PUBLICATIONS

*Applied Spectroscopy*, vol. 40, No. 5, 1986, "A Multisurface Matrix-Isolation Apparatus" by Robert H. Hauge, Leif Fredin, Zakya H. Kafafi, and John L. Margrave, pp. 588 to 595.

*Primary Examiner*—Carolyn E. Fields
*Assistant Examiner*—Constantine Hannaher
*Attorney, Agent, or Firm*—Walter A. Hackler

[57] ABSTRACT

As a means for connecting a gas chromatograph and an IR-spectrometer, devices are used which include a cooled carrier which allows to condensate the substances supplied by the gas chromatograph on its surface where they may be examined by spectroscopy. The examination of a new sample makes necessary the evaporation of the substances condensated on this surface before. Up to now, the heating and the cooling of the carrier which was necessary to this end, took a rather long time. Further, the heating of the carrier was limited to a temperature at which not all substances could be completely eliminated from the surface of the carrier. Now, the invention provides for a thermal decoupling of the carrier from the cooling device. Such decoupling allows to heat the carrier to higher tempreatures and to reduce the time needed for performing a measuring cycle, since as a result of the decoupling the cooling device is not heated but the heating is limited to the small mass of the carrier. A removable coupling may be effected by means of a thermally conducting mechanical connection which may be separated, of a gas stream which may be interrupted, or of moving the carrier from a cooling zone to a heating zone.

14 Claims, 3 Drawing Sheets

DEVICE FOR COLLECTING SAMPLES

The present invention relates to a device for collecting samples to be analyzed by spectroscopic examination, comprising a carrier being movably arranged inside a housing, which is adapted for being evacuated, and provided with a drive and means for introducing its surface into the ray path of the spectrometer, and comprising further a cooling device provided with a cooling head projecting into the housing and being thermally coupled to the carrier, and a nozzle directed upon the surface of the carrier for supplying a sample in the gaseous state for analyzation thereof.

A device of this type, which has been known from U.S. Pat. Spec. No. 4,158,772 serves for coupling a gas chromatograph to an infrared spectrometer. In the case of this known device the carrier, which is provided with a drive, is seated to rotate on a bolt which is thermally coupled to the cooling device and provided with a thread so that any rotary movement of the carrier is accompanied simultaneously by a movement in the axial direction of the thread. The carrier exhibits the shape of an octogonal prism which, due to its rotary movement, is moved into successive positions in which one of the surfaces of the prism faces the nozzle, the latter directing upon the surface of the prism a gas jet containing the substances to be examined which then precipitate on the surface of the carrier in the solid state of aggregation. Due to the axial movement accompanying the rotary movement, spots containing the substances which are to be analyzed are formed on the individual surfaces of the prism in a row, one behind the other in the axial direction.

As mentioned before, the known device serves for examining substances supplied from a gas chromatograph. Gas chromatographs operate with a carrier gas which usually consists of helium and argon mixed at a ratio of, for example, 98.5 to 1.5. In the case of such a gas mixture only the argon will precipitate on the surface of the carrier because the solidifying temperature of helium is never reached, and the argon precipitated on the surface of the carrier forms a matrix in which the substances to be analyzed are embedded. However, it is also possible in this manner to analyze substances which are directly vaporized and supplied to the device either directly or with the aid of a carrier gas and precipitated upon the surface of the carrier.

In any event, the carrier must be free from any other substances when the substances to be analyzed are applied on the surface of the carrier by means of the nozzle. It is, therefore, necessary that all substances previously applied upon the carrier by vaporization be removed before the next analysis. This is achieve by switching off the cooling device so that the device is permitted to assume room temperature. This process, i.e. permitting the device to warm up and any residual substances to vaporize, and cooling down the device thereafter to very low temperatures, normally in the range of 10K, takes many hours in the case of the known devices. In addition, there is always the risk that not all of the substances accumulated on the carrier evaporate fully at room temperature, which may lead to errors in subsequent examinations. On the other hand, it is not possible to apply high temperatures because this might damage the cooling device which must not normally be exposed to temperatures higher than 40° C.

Now, it is the object of the present invention to design a device of the type mentioned above in a manner to accelerate the heating-up and evaporizing process and to reduce thereby the time that has to be waited between the individual measuring cycles. In addition, it is an object of the present invention to ensure complete vaporization of all substances previously accumulated on the carrier without exposing the cooling device to any risk of damage.

This object is achieved according to the invention by an arrangement in which thermal coupling between the carrier and the cooling head of the cooling device can be established and separated as required and in which means for heating the carrier are provided.

The fact that, according to the invention, the thermal coupling between the carrier and the cooling device can be separated provides the possibility to warm up the carrier, without taking care of the cooling device, and to equip the carrier for this purpose with special heating means. Accordingly, the carrier can be heated up much more quickly than heretofore, and even to temperatures in excess of 40° C. so that the device according to the invention can be employed also for analyzing chemical compounds having a higher boiling point, which heretofore could not be removed completely from the surface of the carrier so that their examination was rather problematic. The present invention therefore extends the possible applications of such devices, both as regards the range of substances to be analyzed and as regards the economy of the process which can be increased substantially due to the reduction of the time required for the measuring cycle. As regards the acceleration of the heating-up and cooling-down cycle, it is a factor of considerable importance that the refrigeration machine, being decoupled thermally from the carrier, need not be heated up to a high temperature and then cooled down again, together with the carrier, but may instead remain at cooling temperature so that the masses of the cooling device do not participate in the heating and cooling cycle.

In the known devices, the known carrier is connected with the cooling head in a heat-conductive manner, by mechanical contact. Now, a first embodiment of the invention provides for such a device that the elements establishing the mechanical contact can be disengaged and engaged selectively. For example, the carrier may be mounted on a shaft, and one end of the shaft may engage a bushing provided on the cooling head and comprising sliding contacts engaging the circumference of the shaft. The shaft is arranged for axial displacement so that it can be moved out of the bushing in the axial direction, for separating the heat-conductive connection, and moved back into the bushing. The particular advantage of this arrangement resides in the fact that the drive, which is anyway available and which serves for imparting a rotary and an axial movement to the carrier, may be used also for separating the thermal coupling between the carrier and the cooling head at the end of the measuring cycle.

A preferred method of realizing the thermal coupling is achieved, however, according to a further improvement of the invention by heat transmission through a gas current which is passed through the cooling head and directed upon the carrier and which can be switched on and off selectively. Such a gas current is a very effective heat-transmission agent which is only little inferior to the direct heat-conductive connection, but provides the considerable advantage that no mechanical contacts have to be established and that the thermal coupling can be separated and established again very easily, by switching the gas current on or off, respectively.

According to a preferred embodiment of the invention, when a gas current is used for thermal coupling, it is also provided that the carrier is mounted on a shaft one end of which engages a bushing mounted on the cooling head and receiving in this case the end of a channel extending through the cooling head for guiding the gas current through the annular gap formed between the shaft and the bushing and into a labyrinth system which is delimited, at least partly, by the carrier and whose outlet communicates with the interior of the housing.

As the gas current passes the channel extending through the cooling head, it is cooled down practically to the temperature of the cooling head, the labyrinth system ensuring that the gas current gets into contact with the carrier over a large surface so that in this case, too, the carrier is cooled down relatively quickly to the temperature of the gas. At the same time, the cross-section of the labyrinth system, which leads radially outwardly from the bushing, increases considerably whereby the speed of the gas is slowed down and, accordingly, the dwelling time of the gas in the labyrinth system, which is required to ensure effective heat exchange, is increased. The gas current required for cooling may in this case be limited to a value at which the pump provided for evacuating the housing is capable of maintaining the vacuum required for the respective measurements.

As mentioned before, it is of advantage, irrespective of the nature in which the thermal coupling is realized, if the carrier is mounted on a shaft one end of which engages a bushing provided on the cooling head. Especially in embodiments of the invention of this type, the carrier may advantageously comprise a cylindrical portion with the nozzle being directed radially upon its outside. In addition, the shaft carrying the annular portion may be provided on its one end with a thread engaging a corresponding threaded bushing so that every rotary movement of the shaft will entrain a corresponding axial movement. It is possible in this manner to apply upon the cylindrical portion of the carrier a trace of the substance to be analyzed in the form of a helical line which then reflects the development over time of the substances to be analyzed.

The carrier may, in principle, have any desired shape, and it is generally also imaginable to use a stationary carrier plate across which the nozzle can be guided according to a predetermined pattern. If movable carriers are used, they may, for example, also comprise a disk-shaped portion instead of the cylindrical portion, in which case the nozzle may be movable radially relative to the disk. According to another embodiment of the invention, the carrier is formed by an endless tape guided on two rollers, one of the rollers being thermally coupled with the cooling head, and the other one being arranged in the area of the heating system. Provided the tape exhibits sufficiently poor conductivity, the degree of thermal decoupling between the two rollers will be sufficiently high to ensure at least that the roller which is thermally coupled to the cooling head will not heat up to inadmissibly high temperatures when the tape is heated in the area of the other roller. It may be convenient in this case to provide that the tape comprises alternating portions of high and poor heat-conductivity, in which case the portions exhibiting high heat-conductivity, i.e. which cool down and heat up readily, serve as carrier for the substances to be analyzed, while the portions exhibiting poor heat conductivity ensure that the highly conductive portions are insulated effectively from each other.

The means for heating the carrier may have any desired design. In particular, electric heating installations of any type may be used for this purpose. It has, however, been found to be particularly convenient to use a source of intense heat radiation directed upon the carrier as such a source can be accommodated outside the housing of the device and directed upon the carrier through a window. This arrangement would also permit to irradiate the substances applied to the carrier directly so that the transmission of heat to the carrier itself and, thus, the heat load on the device, is reduced to a minimum. This would load to a further reduction of the time required for evaporizing the substances and cooling the carrier down subsequently to operating temperature. In this respect, it may also be of advantage if at least part of the surface of the arrangement comprising the carrier and the cooling device is blackened.

As mentioned before, in order to achieve the desired acceleration of the operating cycle, it is important also that the masses that have to be subjected to the heating cycle are reduced. Consequently, it is of considerable interest to make the carrier as small as possible. However, the surface of the carrier required for each measuring cycle is dependent, among other things, on the size of the surface required for accommodating a part of the sample that can be separated from other parts and, accordingly, analyzed separately. In addition, the test sensibility rises considerably as the size of the surface element on which the substances to be analyzed are concentrated reduces, the size of the surface element being in turn dependent on the optical system by which the light beam used for spectroscopy is directed upon the sample carrier, the optical system determining the size of the focal spot on the carrier and, thus, the size of surface portions that can be insulated from each other. It therefore helps achieve the objectives of the invention if the device is provided with optical systems permitting to produce on the surface of the carrier a very small focal spot, with very high accuracy. Consequently, it is provided according to one preferred embodiment of the invention that at least one optical system is arranged on the housing which permits a light beam of a spectrometer to be focussed upon the surface of the carrier and an image of the focus to be projected into the detector system of the spectrometer, and that this optical system is arranged in a holder connected to the housing and provided with a window between the system and the carrier which closes the housing. The described optical system may, advantageously, be designed in the form of a Cassegrain system. Although one common optical system is sufficient to guide both the incoming and the reflected beams, it is also possible to provide two such systems in two tubular pipe sections arranged on the housing and closed towards the interior of the housing by a window.

Other details and embodiments of the invention will be apparent from the following description of the embodiments shown in the drawing. The features that can be derived from the specification and the drawing may be incorporated in other embodiments of the invention either individually or in any combination thereof. In the drawing FIG. 1 shows a longitudinal section through a first device according to the invention, without the nozzle and its holding means;

Figure 1:
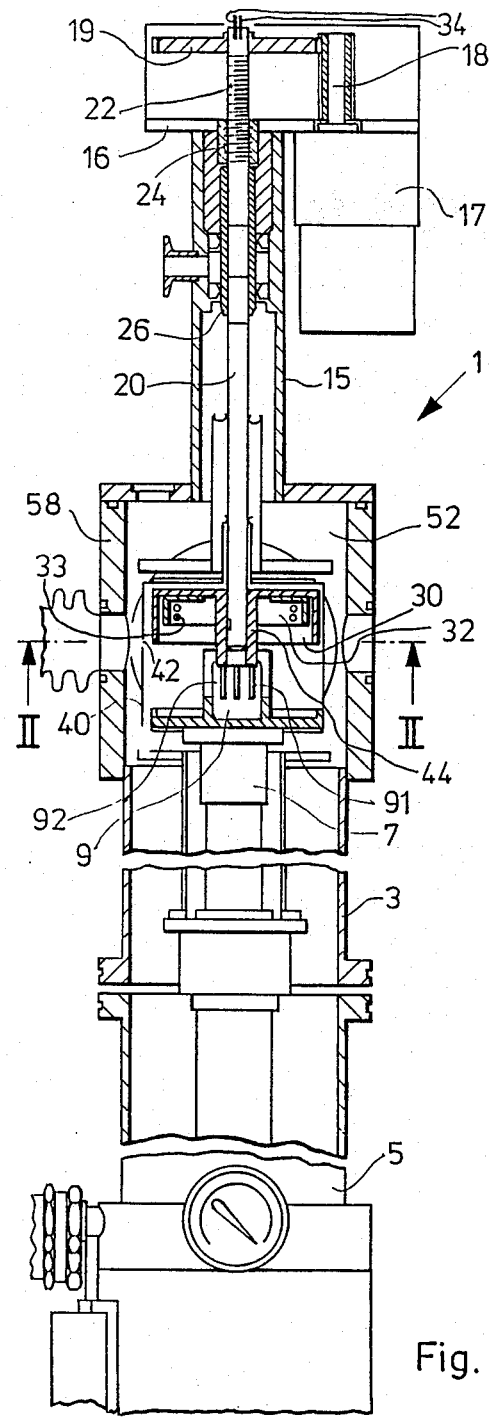

The device 1 shown in FIG. 1 comprises a substantially column-shaped housing 3 with a cooling device 5 arranged in its lower portion. The cooling device comprises a cooling head 7 which is arranged inside the housing 3 and which can be cooled down to, and maintained at, a predetermined low temperature, for example to a temperature of 10K. A bushing fixed on the cooling head 7 is provided at its end with axial slots 91 whereby separate sliding contacts 92 are formed which may be brought into resilient engagement with the circumference of a part introduced into the bushing 9. The column-shaped housing 3 comprises an upper pipe 15 carrying on its upper end a plate 16 with a geared motor 17 mounted thereon. The power take-off shaft of this geared motor 17 carries a pinion 18 which meshes with a gear 19 mounted on the upper end of a shaft 20 to rotate therewith. A portion of the shaft neighboring the gear 19 is provided with a thread 22 engaging a threaded bushing 24 arranged on the upper end of the pipe 15. In the area following the thread 22, the shaft is passed through a vacuum bushing 22 provided in the pipe 5 and imparting at the same time to the shaft 20 exact axial alignment. Fixed to the lower end of the shaft 20 is a carrier 30 which is designed substantially in the form of a hollow cylinder of circular cross-section and whose cylindrical outer surface is adapted for receiving the sample to be analyzed. Inside the cylindrical carrier 30, there is provided a concentrical cylindrical heating carrier 32 with a heating winding 33 the electric connections 34 of which are passed through the shaft 20 which takes the form of a tube. The ends of these connections projecting from the upper end of the hollow shaft are connected to slip rings which are not shown in the drawing and by which an electric current can be supplied to the heating winding.

The carrier 30 is enclosed by a case 40 made of nickel-plated sheet copper and forming a protection against radiation which screens the carrier 30 largely against heat irradiated from the outside. The case 40 is provided with a bore 42 which accommodates the nozzle 42 shown in FIG. 4 in such a manner that its orifice is positioned at a small distance of the surface of the cylindrical carrier 30.

The carrier 30 is mounted on the shaft 20 by means of a pipe section 44 which in the position of the carrier 30 shown in FIG. 1 is just in engagement with the bushing 9 so that the sliding contacts 92 come into engagement with the outer surface of the pipe section 44 near its lower edge. The sliding contacts 92 of the bushing 9, therefore, provide a heat-conductive connection between the cooling head 7 and the bushing 44 which can be regarded as part of the shaft 20 on which the carrier 30 is mounted. When the shaft 20 is rotated by means of the geared motor 17 so that the thread 22 provided at the upper end of the shaft 20 is screwed out an additional amount from the threaded bushing 24 at the upper end of the pipe 15, then the pipe section 44 on the lower end of the shaft 20 is raised a little further so that it comes out of engagement with the sliding contacts 92. This interrupts the thermal coupling between the cooling head 7 and the carrier 30 so that the carrier 30 can be heated up quickly by switching on the heating winding 33, without any danger for the cooling device 5 and the cooling head 7, and this even when the carrier assumes temperatures far above the temperature of 40° C. maximally admissible for such a cooling device. It is an additional advantage in this connection that the whole cooling device, including the cooling head 7, can be maintained at the normal operating temperature so that there is no need for heating up, and cooling down later, the whole mass of the cooling device during every measuring cycle and only the small mass of the carrier 30 has to be subjected to such a heating and cooling cycle.

After all substances that have been applied upon the surface of the carrier during the preceding measuring cycle have been vaporized by heating up the carrier, the device is ready for the next measuring cycle. The motor 17 is then switched on again to rotate the shaft 20 in the sense in which the threaded bushing 24 is screwed in until the shaft 20 and the carrier 30 have reached their lowermost position in which the shaft 20, with the pipe section 44 fixed thereon, projects far into the bushing 9 on the cooling head 7 and the upper edge of the cylindrical outer surface of the carrier 30 occupies a position opposite the bore 42 in the radiation screen 40 through which the substance to be analyzed can be applied upon the surface of the carrier by means of a nozzle, while the shaft 20 is driven again slowly by the geared motor 17 so that the cylindrical outer surface of the carrier is slowly rotated past the nozzle and, at the same time, moved upwards in the vertical direction. The nozzle, therefore, describes a helical line on the outer face of the cylindrical carrier 30 along which the gas supplied by the nozzle is applied upon the carrier where it condenses due to the low temperature of the carrier.

Figure 2:
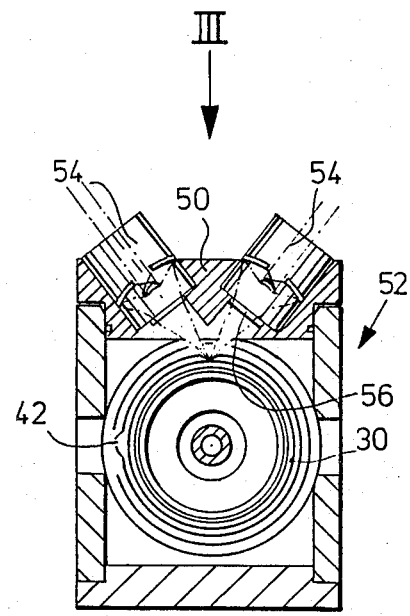
FIG. 2 shows a section along line II—II through the device of FIG. 1.
Figure 3:
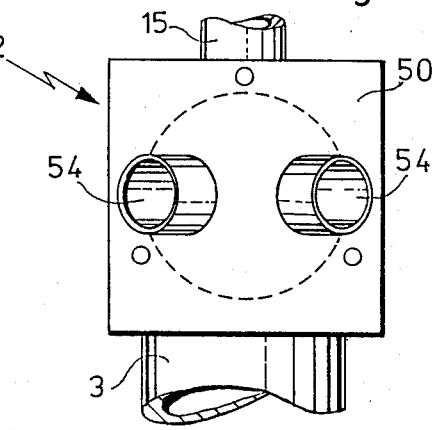
FIG. 3 is a view of the central portion of the device according to FIG. 1, in the direction indicated by arrow III in FIG. 2.

The substances condensed on the surface of the carrier can be analyzed by spectroscopic methods. A spectroscope comprises optical means for projecting a light beam upon the substance to be analyzed and for projecting the light reflected by the substance and/or the carrier 30 after penetration of the substance upon a detector. As can be seen in FIG. 2, the device according to FIG. 1 comprises optical members permitting an extremely small area of the surface of the carrier 30 to be examined. As can be seen in FIG. 2, the part 52 of the housing accommodating the cooling head 7 and the carrier 30 comprises a flange 50 with two pipe sections 54 accommodating each a Cassegrain system.

The focal points of both Cassegrain systems coincide at the same point of the surface of the carrier 30, the said point being offset by 90° in the circumferential direction, relative to the bore 42 of the nozzle serving for supplying the gaseous substances. Accordingly, a substance having been applied by the nozzle upon the surface of the carrier 30 will arrive at the position of the focal points of the Cassegrain systems after a revolution of the carrier 30 by 90°. Due consideration has been given in this connection to the fact that during rotation the carrier has moved also in the axial direction, due to the thread 22, 24. The pipe sections 54 are sealed off vacuum-tight by plane parallel, optically permeable plates 56, and are mounted on the flange 50 in a vacuum-tight manner so that the parts of the Cassegrain systems arranged inside the pipe sections are outside of the vacuum prevailing inside the housing part 52. This enables these optical systems to be mounted, adjusted and, if necessary, serviced with particular ease.

Figure 4:
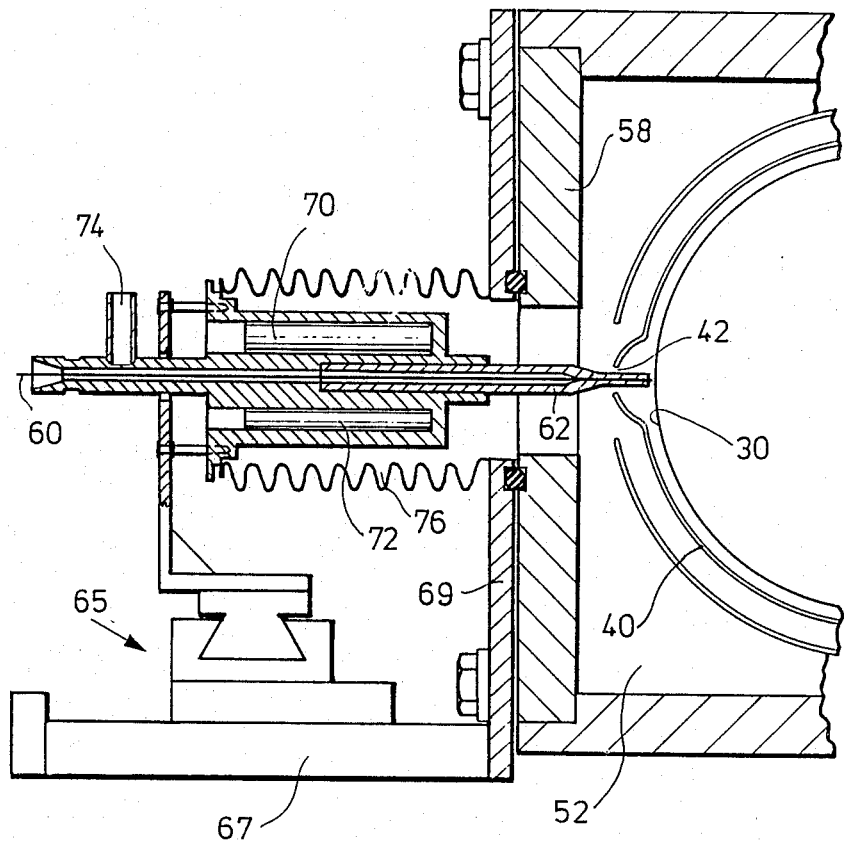
FIG. 4 shows enlarged representations, partly as a side view and partly as section, of a nozzle arrangement of the device according to the invention of the type that may be arranged in the device according to FIG. 1, in plane II—II.

FIG. 4 shows an enlarged representation of a nozzle arrangement of the type suited for the device according to FIG. 1. The holding means for the nozzle, which serves to supply to the carrier the gas containing the substances to be analyzed, is mounted on the left side wall 38 of the housing part 52, as viewed in FIG. 1. While the gas itself may consist of the substances to be analyzed, it may also be a gas mixture comprising the substances to be analyzed in a carrier gas, as in the case of the eluate of a gas chromatograph. The nozzle as such is formed by the end of a capillary tube 60 of quartz glass which is arranged inside a nozzle carrier 62 and which ends in the immediate neighborhood of the surface of the carrier 30. The nozzle carrier 62 extends through the bore 42 of the before-mentioned case 40. The diameter of the bore 42 is larger than the diameter of the nozzle carrier 62 to enable the nozzle carrier 62 to be displaced relative to the carrier 30, in particular in parallel to its axis of rotation. The displacement of the nozzle carrier 62 parallel to the axis of rotation of the carrier 30 and radially to the axis of rotation of the carrier 30 is achieved by means of a cross-table 65 fastened to a mounting plate 67 which is in turn mounted on a plate 69 screwed to the side wall 58. A heating cartridge 70 is arranged in a corresponding bore inside the nozzle carrier 62, on one side of the bore accommodating the capillary tube 60, and serves to heat up the nozzle carrier 62 to a temperature of approx. 200° C. in order to prevent any substances which are not easily volatelized, of the type that may be found in the eluate of a gas chromatograph, from depositing in the capillary tube 60. Another bore provided in the nozzle carrier 62 on the side of the capillary tube opposite that of the heating cartridge 50 accommodates a temperature sensor 72 for monitoring and controlling the temperature of the nozzle carrier 62. A connection 74 for a stabilizing vacuum leads to a pump. A vacuum-tight bellows 76 arranged between the nozzle carrier 62 and the plate 79 permits the before-described movements of the nozzle carrier, while preventing any air from penetrating into the housing part 52 along the outside of the nozzle carrier 62.

The Cassegrain systems arranged in the pipe sections 54 are, for example, part of an infrared spectrometer serving for analyzing the substances applied to the surface of the carrier 30. As has been mentioned before, the described device may serve for analyzing the eluate of a gas chromatograph. Such eluate consists of a carrier gas containing usually 98.5% helium and 1.5% argon and carrying with it the substances of interest which are to be analyzed. Due to the extremely low boiling point of helium, only the argon component of the carrier gas, with the substances contained therein, will condense on the surface of the carrier, forming on the latter a matrix in which the other substances are embedded. It is then possible to analyze these substances by spectroscopic methods, in particular by FT-IR spectroscopy.

The invention does not only increase substantially the speed at which such analyses can be carried out, but permits in the use of high temperatures for vaporizing the previously analyzed substances, thus ensuring a very high degree of purity which in turn makes it desirable to increase the sensitivity of the measuring device in such a manner that chemical compounds in the picogram range can be analyzed, while heretofore it was possible only to carry out examinations down to the nanogram range. This increase in sensitivity is achieved by a corresponding improvement of the optical systems whereby the focal point of the optical systems is rendered so small that the quantity of substance found in the area of the focal spot is in the picogram range. It is necessary for this purpose to adjust the optical systems which are required for supplying the measuring radiation, in particular the IR light, and for projecting the reflected light upon a detector arrangement, to a common focal spot located on the surface of the carrier. This adjustment can be effected with the necessary extreme accuracy only when the carrier and the optical systems form a single unit, as in the case of the embodiment of the invention.

The cylindrical carrier 30 of the described example has an outer diameter of 8 cm and a height of 3 cm. The carrier consists of copper and has a polished, gold-plated cylindrical outer surface. The resilient bushing 9, which surrounds the lower end of the shaft 20, supports the carrier safely, ensuring thereby very exact positioning of the carrier 30. However, it would also be possible, for example, to arrange special wipers inside the bushing, which wipers have to be very soft so that they do not influence the position of the carrier 30 if this type of support should lead to overdetermination or if the position of the cooling head with the bushing cannot be adjusted with the necessary accuracy. Such springs may consist, for example, of a copper-beryllium alloy and be silver-plated.

In the case of described embodiment it was possible to perform the steps of heating up the carrier to 200° C., after decoupling from the cooling head, cooling it down thereafter to room temperature and, after establishment of the thermal coupling to the cooling head, further to operating temperature, within two hours. As compared to this, such a cycle required approximately 10 hours with the known devices, and in addition the temperature of the carrier was not permitted to exceed 40° C. during this cycle.

Figure 5:
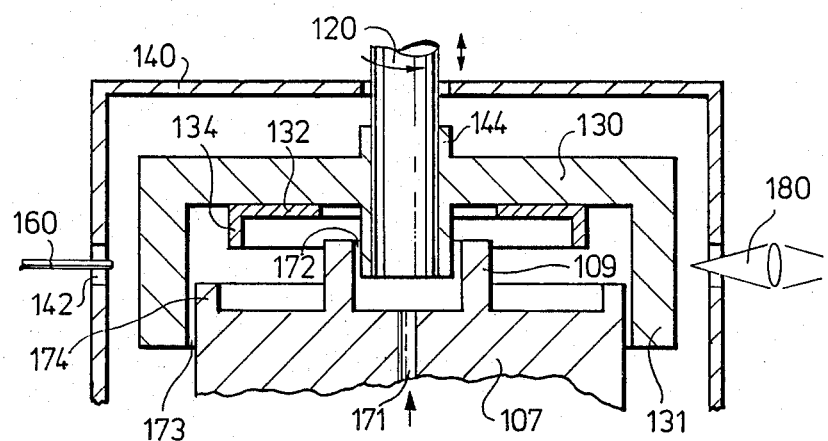
FIG. 5 shows a longitudinal section through the central portion of another device according to the invention, in enlarged scale compared with FIG. I.

FIG. 5 illustrates one embodiment of the device according to the invention where the thermal coupling between the cooling head 107 and the carrier 130 is not effected by heat transmission via mechanical contact, but by means of a gas current. Similar to the embodiment shown in FIG. 1, the device shown diagrammatically in FIG. 5 comprises a carrier 130 mounted on the lower end of a shaft 120, the end of which engages a bushing 109 arranged on the upper end of the cooling head 107. The carrier 130 is again mounted on the lower end of the shaft 120, via a pipe section 144, and comprises a cylindrical surface upon which the substances to be analyzed can be applied by means of a nozzle 160 which is indicated only diagrammatically. The shaft 120 can be driven in the same manner as explained in connection with FIG. 1. Here again, the carrier 130 is surrounded by a case 140 serving as a heat screen and comprising a bore 142 serving as a passage for the nozzle 160. The heating carrier 132 is arranged on the inside of the carrier 130.

As mentioned before, the thermal coupling between the cooling head 107 and the carrier 130 is realized in this case by means of a gas current which is passed through a central bore 171 in the cooling head 107, which enters the space enclosed by the bushing 109 at a central point and which impinges upon the end of the shaft 120 and the pipe section 144. The end of the shaft 120 and the pipe section 144 is tightly enclosed by the bushing 109 so that a narrow gap 172, which has to be passed by the heat exchanger gas, is formed between the bushing 109 and the pipe section 144. The gas then gets into contact with the central portion of the carrier 130, inwardly of the heating carrier 132, so that this part of the carrier 30 is already cooled. In addition, the cylindrical portion 131 of the carrier 130 surrounds the cylindrical cooling head 107 at a small distance so that here, too, a narrow gap 173 is formed which is delimited by the carrier 130 and which serves as a way out for the heat exchanger gas. The gas flow is deflected two more times on its way between the gap 132 surrounding the shaft 120 and the gap 123 between the cylindrical portion 131 of the carrier and the cooling head 107, due to a cylindrical rim 134 provided on the heating carrier 132 and another cylindrical rim at the circumference of the cooling head 107. One thus obtains a labyrinth which is defined on one side by the carrier 130 so that the gas emerging from the central channel 171 of the cooling head 107, which has been cooled down to the temperature of the cooling head 107, is forced to flow past the carrier 130 along a relatively long path whereby very intense heat exchange takes place between the gas and the carrier 130. It is particularly advantageous in this connection that the gas is also in constant thermal contact with the cooling head 107 so that here again constant heat exchange takes place and the heat absorbed by the cooling gas is transmitted immediately to the cooling head 107. Accordingly, very effective cooling of the carrier 130 is obtained, with the result that the carrier is cooled down to the temperature of the cooling head 107 within relatively short time. The quantity of the gas serving as heat-exchanging agent is so small that it can be pumped off without any difficulty by the vacuum pump connected to the housing of the device.

It is easily apparent that the described thermal coupling between the cooling head 107 and the carrier 130 can be interrupted by switching off the gas current serving as heat-exchanging agent. The thermal radiation, which is very low in particular at low temperatures, does not by any means suffice to cause substantial heating-up of the cooling head 107 when the carrier 130 is heated by means of the heating arrangement 132. It should be noted also in this case that the carrier 130 is heated up at the moment when the carrier 130 occupies the position most remote from the cooling head 107 and when, accordingly, the least radiating coupling exists between these two components. There is, therefore, no risk of the cooling head 107 assuming an excessive temperature. Rather, the cooling device may be maintained in operation so that the whole cooling device remains at a low temperature and effective cooling of the carrier 130 is commenced immediately when the carrier 130 is moved into its lowermost position, which is the closest to the cooling head 107, and the gas current serving as heat-exchanging agent is switched on again.

In the embodiment shown in FIG. 5, a light source is indicated diagrammatically at 180. The light source 180 is directed upon the circumference of the carrier 130 and may, instead of the heating carrier, serve to directly heat up and, accordingly, vaporize the substances present on the surface of the carrier 130.

Figure 6:
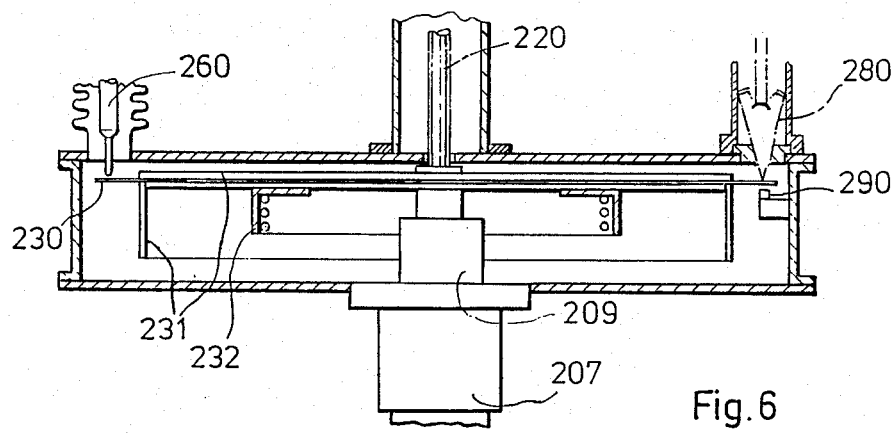
FIG. 6 shows a partial section through another embodiment of a device designed according to the invention and comprising a disk-shaped carrier.

FIG. 6 shows another embodiment of a device according to the invention comprising a disk-shaped carrier 230. The carrier 230 is formed by an annular disk made of silicon, whose inner edge is fastened to a metallic supporting structure 231. The latter in turn is fastened at the lower end of a shaft 220 and provided on its lower face with a heating carrier 232. The lower end of the shaft 222 interacts again with a bushing 209 mounted on the upper side of the cooling head 207. The design of the embodiment according to FIG. 6 conforms insofar with that of the embodiment according to FIG. 1.

The carrier 230 for the substances to be analyzed is formed by that portion of the annular disk which projects beyond the supporting structure 231. Accordingly, a nozzle 260 is provided which is directed vertically upon this portion of the carrier 230 and which, therefore, extends in parallel to the shaft 220. As the silicium disk formed by the carrier 230 is permeable to IR radiation, this embodiment of the invention permits measurements of spectra by transmission. There is provided for this purpose, at a point which is offset at an angle relative to the nozzle 262, an optical system 280 projecting upon the carrier 230 a vertical IR beam supplied from a spectrometer, while an IR detector 290 is provided on the other side of the carrier 230, opposite the optical system 280, for generating a signal proportional to the intensity of the IR radiation which penetrates the sample substances deposited on the carrier 230.

In the case of this arrangement, an annular trace of the substance to be analyzed is formed on the carrier 230 when the disk-shaped carrier is rotated about its axis defined by the shaft 220. If the length of this track is to be equal to a multiple of the length of one revolution, the nozzle 260 as well as the optical system 280 and the detector 290 can be displaced radially to the disk-shaped carrier 230, by means of an arrangement similar to that shown in FIG. 4, so that the substances applied form a helical line which can then be scanned by means of the IR radiation supplied by the optical system 280, and the detector 290.

In the case of this embodiment of the invention, thermal coupling between the carrier 230 and the cooling head 207 is effected by a gas current as has been explained in greater detail in connection with FIG. 2. The use of a gas current is particularly advantageous in this case because it does not require any change of the axial position of the carrier 230, for separating and reestablishing the thermal coupling. Any change of the position of the carrier 230 in the axial direction would be little desirable in the case of the embodiment of FIG. 6 because the nozzle 260 as well as the optical system 280 and the detector 290 would have to follow any such change. On the other hand, it is absolutely imaginable that thermal coupling may be established by heat-conductive contact, and interrupted again, by an arrangement in which the entire cooling device, together with the cooling head 208, is adapted for being displaced relative to the carrier 230 and its drive, of which the shaft 220 forms a part, and the remaining installations.

Figure 7:
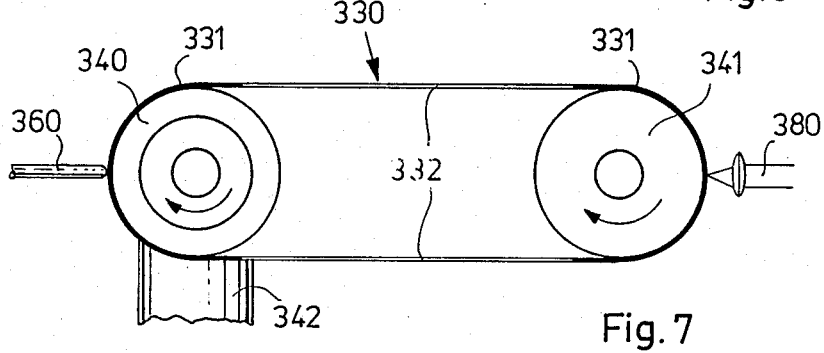
FIG. 7 is a diagrammatic side view of those parts of another device according to the invention which are essential for the invention.
Figure 8:
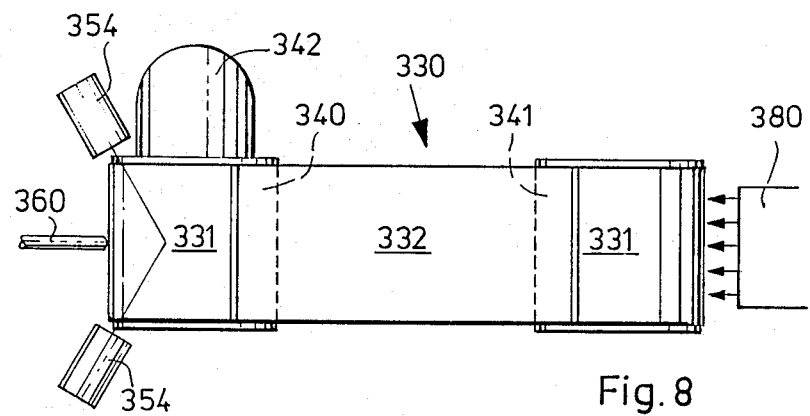
FIG. 8 shows a top view of the arrangement of FIG. 7.

In the embodiments shown in FIGS. 7 and 8, the carrier 330 is formed by a tape guided on two rollers 340, 341. One of these rollers 340 is seated on a cooling head which is connected to a cooling device—not shown in detail—via a line 342. In the area of the cooled roller 340 one can see again a nozzle 360 through which gaseous sample substances are supplied and applied upon the surface of the carrier 330 so that the sample substances condense thereon and are then available for analysis. The nozzle 360 is movable in the axial direction of the roller 340 so that the sample substances that have condensed on the surface of the carrier 330 form lines parallel to the axis. By advancing the tape-shaped carrier 330 gradually it is, therefore, possible to produce on the tape a pattern of parallel stripes. Advancing the tape slowly and continuously would produce a corresponding zig-zag line.

The analysis of the substances applied is again effected by an infrared spectrometer whose radiation is focussed upon the surface of the carrier 330 by two Cassegrain systems 354. The arrangement may be similar to that of FIG. 2. In addition, the nozzle 360 and the optical system 354 may be arranged in a common slide so that both elements can be moved in synchronism in a direction parallel to the axis of the roller 340.

In the area of the other roller 341, a carrier 330 can be heated up in order to remove the substances precipitated on the carrier, by vaporization. To this end, a light source 380 is provided by which light of sufficient energy can be projected upon the surface of the carrier 330 for heating up the substances and the carrier to a temperature at which complete vaporization of the substances is guaranteed. The temperatures reached may be far above ambient temperature.

Thermal decoupling between the portion of the carrier 330, which has been heated up to a high temperature, and the cold area of the carrier is achieved in this case by the fact that the tape-shaped carrier 330 exhibits alternating sections 313 and 332 of very good conductivity on the one hand and very poor thermal conductivity on the other hand. The sections 331 exhibiting good thermal conductivity which in the illustrated embodiment occupies a position in which they are guided around the rollers 340, 341 symmetrically, are thermally insulated from each other by the intermediate sections 332 of poor thermal conductivity so that heating-up of the one section which is exposed to the radiation source 380 does not have any effects on the temperature of the other section 331 which passes around the other roller. Due to their good thermal conductivity, these sections assume an identical temperature practically over their whole size, and due to their low mass they assume very rapidly the low temperature of the cold roller or, on the other hand, the high temperature required the the vaporization process. Accordingly, the time required for applying the sample on one section and for analyzing it will be normally sufficient for vaporizing the substances on the other section 333 which were analyzed before. A device of this type, which is shown in the drawing only very diagrammatically but which can be implemented in practice without any difficulty, therefore permits almost continuous operation.

It is understood that the invention is not limited to the embodiment shown. Rather the broad range of examples show that the man of the art has many possibilities of implementing the invention.

We claim:

1. Device for collecting samples to be analyzed by spectroscopic examination, comprising a carrier being movably arranged inside a housing, which is adapted for being evacuated, and provided with a drive and means for introducing its surface into the ray path of the spectrometer, and comprising further a cooling device provided with a cooling head projecting into the housing and being thermally coupled to the carrier, and a nozzle directed upon the surface of the carrier for supplying a sample in the gaseous state for analization thereof, characterized in that thermal coupling between the said carrier and the said cooling head of the cooling device can be established and separated as required and that means for heating the said carrier are provided.

2. Device according to claim 1, characterized in that the said carrier is connected with the said cooling head in a heat-conductive manner, by mechanical contact, and that the elements establishing the mechanical contact can be disengaged and engaged selectively.

3. Device according to claim 2, characterized in that the said carrier is mounted on a shaft and one end of the said shaft engages a bushing provided on the said cooling head, that the said bushing comprises sliding contacts engaging the circumference of the said shaft and that the said shaft is arranged for axial displacement so that it can be moved out of the said bushing in the axial direction, for separating the heat-conductive connection, and moved back into the said bushing in the reverse sense.

4. Device according to claim 2, characterized in that the said carrier is formed by an endless tape guided on two rollers, one of the said rollers being thermally coupled with the said cooling head, and the other one being arranged in the area of the said heating system.

5. Device according to claim 4, characterized in that the said tape comprises alternating portions of high and poor heat-conductivity.

6. Device according to claim 1, characterized in that the said carrier is thermally coupled to the said cooling head by means of a gas current which is passed through the said cooling head and directed upon the said carrier and which can be switched on and off selectively.

7. Device according to claim 6, characterized in that the said carrier is mounted on a shaft one end of which engages a bushing mounted on the said cooling head and that the said bushing receives the end of a channel extending through the said cooling head for guiding the said gas current through the annular gap formed between the said shaft and the said bushing and into a labyrinth system which is delimited, at least partly, by the said carrier and whose outlet communicates with the interior of the said housing.

8. Device according to claim 1, characterized in that the said carrier comprises a cylindrical portion with the said nozzle being directed radially upon its outside.

9. Device according to claim 8, characterized in that the said cylindrical portion of the said carrier is mounted on a shaft provided on its one end with a thread engaging a corresponding threaded bushing so that every rotary movement of the said shaft will entrain a corresponding axial movement.

10. Device according to claim 1, characterized in that the installation for heating the said carrier comprises a source of intense heat radiation directed upon the said carrier.

11. Device according to claim 1, characterized in that the said nozzle is adapted for being adjusted in relation to the said carrier, at least in one direction.

12. Device according to claim 1, characterized in that at least one optical system is arranged on the said housing which permits a light beam of a spectrometer to be focussed upon the surface of the said carrier and an image of the focus to be projected into the detector system of the said spectrometer, and that this optical system is arranged in a holder connected to the said housing and provided with a window between the system and the said carrier for closing the said housing.

13. Device according to claim 12, characterized in that the said optical system is designed in the form of a Cassegrain system.

14. Device according to claim 12, characterized in that the said housing is provided with two tube sections which are closed towards the interior of the said housing by a window, whose axes are directed towards the same point of the said carrier and which accommodate each an optical system focussed upon the said point.

* * * * *